United States Patent [19]

Kobayashi et al.

[11] Patent Number: 4,991,584
[45] Date of Patent: Feb. 12, 1991

[54] OPHTHALMIC EXAMINING APPARATUS AND METHOD CAPABLE OF EXAMINING GLAUCOMA

[75] Inventors: Kazunobu Kobayashi, Yokohama; Isao Matsumura, Yokosuka, both of Japan

[73] Assignee: Canon Kabushiki Kaisha, Tokyo, Japan

[21] Appl. No.: 403,018

[22] Filed: Aug. 31, 1989

Related U.S. Application Data

[63] Continuation of Ser. No. 108,814, Oct. 15, 1987, abandoned.

[30] Foreign Application Priority Data

Oct. 25, 1986 [JP] Japan .................. 61-254064
Oct. 25, 1986 [JP] Japan .................. 61-254066
Nov. 15, 1986 [JP] Japan .................. 61-272072
Dec. 6, 1986 [JP] Japan .................. 61-290744

[51] Int. Cl.$^5$ ............................................. A61B 3/16
[52] U.S. Cl. ................................ 128/648; 128/652; 351/211

[58] Field of Search ........... 128/648, 652, 645, 646, 128/647, 649, 650; 351/206, 205, 211

[56] References Cited

U.S. PATENT DOCUMENTS

| | | | |
|---|---|---|---|
| 3,585,849 | 6/1971 | Grolman | 128/648 |
| 3,832,890 | 9/1974 | Grolman et al. | 128/648 |
| 4,665,923 | 5/1987 | Kobayashi | 128/648 |
| 4,705,045 | 11/1987 | Nishimura | 128/648 |

FOREIGN PATENT DOCUMENTS 2252313 5/1973 Fed. Rep. of Germany ...... 128/648

Primary Examiner—Max Hindenburg
Assistant Examiner—J. P. Lacyk
Attorney, Agent, or Firm—Fitzpatrick, Cella, Harper & Scinto

[57] ABSTRACT

An ophthalmic examining apparatus which is provided with at least non-contact type eye pressure measuring means and eye fundus observation means for observing the fundus of an eye to be examined and which is capable of examining glaucoma from eye pressure information and eye fundus image information.

23 Claims, 7 Drawing Sheets

OPHTHALMIC EXAMINING APPARATUS AND METHOD CAPABLE OF EXAMINING GLAUCOMA

This application is a continuation of application Ser. No. 108,814 filed Oct. 15, 1987, now abandoned.

BACKGROUND OF THE INVENTION

1. Field of the Invention

The present invention relates to an ophthalmic examining apparatus and an ophthalmic examining method capable of examining eye pressure and eye fundus image information, particularly, the ratio of the diameter of the disk cup and the diameter of the disk.

2. Related Background Art

In the examination of glaucoma which may often result in loss of eyesight, the measurement of eye pressure and the measurement of eye fundus image information, particularly, the C/D ratio, are said to be effective. The C/D ratio is the ratio of the diameter dimension of the cup (abbreviated as C) created inside the eye fundus disk (abbreviated as D) to the diameter dimension of the eye fundus disk, and D is a numerical value inherent to an eye to be examined, while C is said to be a parameter indicative of the advanced state of glaucoma.

In the conventional measurement, the eye pressure is measured by a non-contact type eye pressure meter known, for example, from U.S. Pat. No. 3,585,849 and the C/D ratio is measured as by measuring the dimension on a film photographed by an eye fundus camera.

SUMMARY OF THE INVENTION

It is an object of the present invention to provide an ophthalmic examining apparatus which is capable of examining a plurality of bits of information regarding glaucoma by a single apparatus.

It is another object of the present invention to provide an ophthalmic examining apparatus which is capable of examining eye pressure information and eye fundus image information without using a pupil dispersing agent.

It is still another object of the present invention to provide an ophthalmic examining apparatus which enables the image of the eye fundus to be observed without any harmful light even if an objective lens opposed to an eye to be examined is used for the illumination of the eye fundus and for the observation of the eye fundus where the objective lens is provided with a hole for blowing fluid therethrough.

It is yet still another object of the present invention to provide an ophthalmic examining method which is capable of accomplishing the measurement of the C/D ratio and the measurement of the value of the eye pressure more quickly.

DESCRIPTION OF THE PREFERRED EMBODIMENTS

Figure 1:
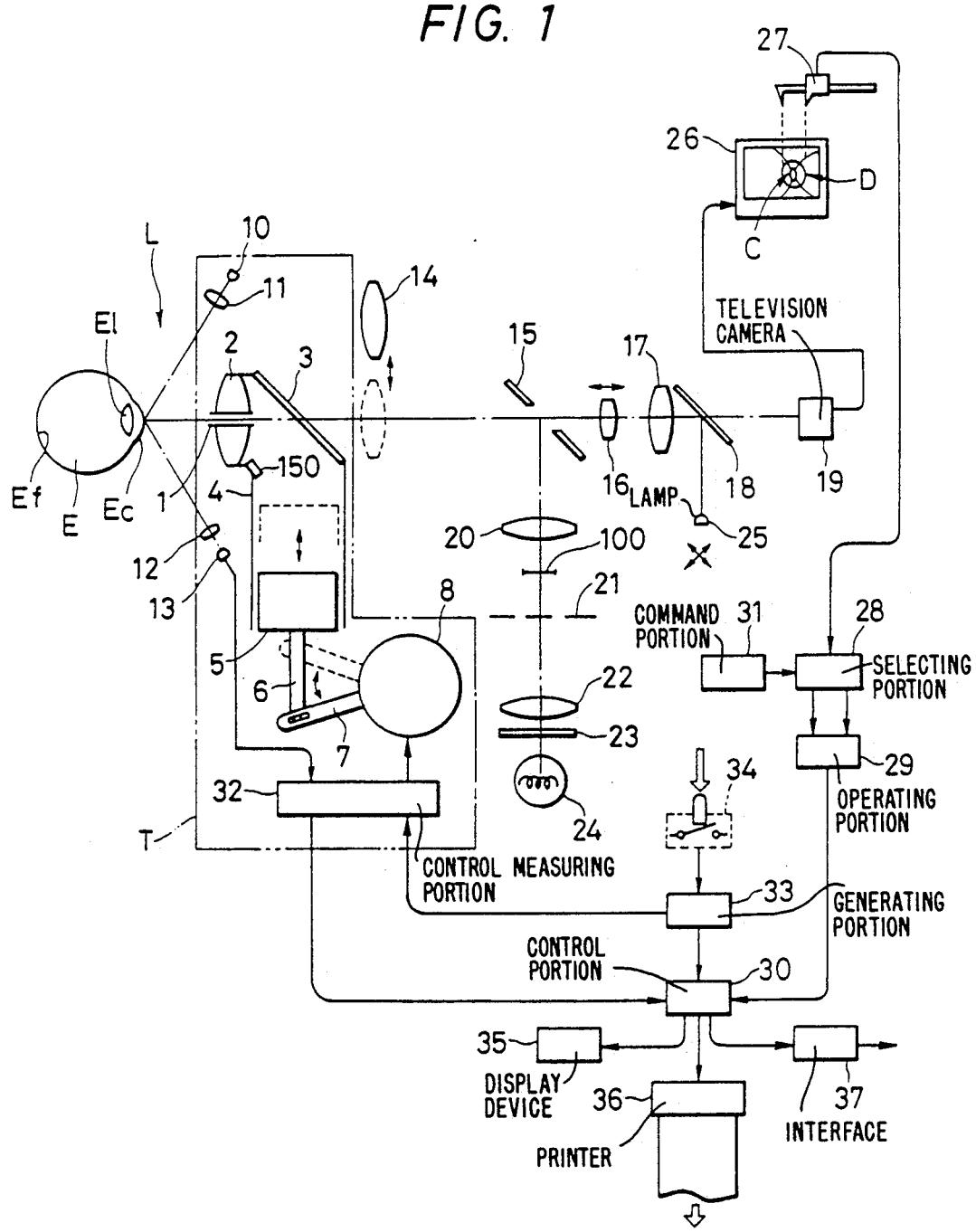
FIG. 1 shows the construction of an embodiment of the present invention.

Referring to FIG. 1 which shows the construction of an embodiment of the present invention, letter E designates an eye to be examined and letter T denotes a non-contact eye pressure meter. The non-contact eye pressure meter T has an objective lens 2 opposed to the eye E to be examined and having a nozzle 1 on the optic axis, a transparent window glass 3 disposed rearwardly thereof and a cylinder 4 connected thereto. A piston 5 is inserted in the cylinder 4 and is adapted to be operated by a rotatable plunger 8 through a rod 6 and an arm 7. A pressure sensor 150 is provided in the cylinder 4. A projection light source 10 is disposed obliquely forwardly of the eye E to be examined, and the emergent light from the light source 10 is projected onto the cornea Ec of the eye E to be examined via a projection lens 11, and the reflected light therefrom may be received by a light-receiving element 13 via a light-receiving lens 12.

Behind the objective lens 2 and the window glass 3, there are successively disposed an observation lens 14 for observing the front eye part retractable out of the optical path, an apertured mirror 15 provided with an opening on the optic axis, a focusing lens 16, an imaging lens 17, a light divider 18 and a television camera 19. On the reflection side of the apertured mirror 15, there are successively disposed a relay lens 20, a light-intercepting plate 100 conjugate with the end of the nozzle 1 which is adjacent to the apertured mirror 15 with respect to a relay lens 20, a ring slit plate 21 having a ring-shaped opening, a condenser lens 22, an infrared filter 23 and an observation light source 24. Further, on the reflection side of the light divider 18, there is provided a fixation lamp 25 movable in any direction in a plane perpendicular to the optic axis.

The output of the television camera 19 is connected to a television monitor 26 so as to project the image of the fundus of the eye E to be examined thereon, and for example, measuring means 27 comprising slide calipers with an electrical output is prepared for measuring the region of the image of the eye fundus. The output of this measuring means 27 is supplied to a data selecting portion 28 and is connected to a data output control portion 30 through an operating portion 29, and a command signal from a command portion 31 is also connected to the data selecting portion 28. The output of the light-receiving element 13 is connected to the data output control portion 30 through the control measuring portion 32 of the non-contact eye pressure meter T, and the output of an eye pressure measuring switch 34 is further connected to the data output control portion 30 through a command generating portion 33. The command generating portion 33 is adapted to output a command signal for operating the rotatable plunger 8 through the control measuring portion 32 of the non-contact eye pressure meter T. Information signals are output from the data output control portion 30 to a display device 35, a printer 36 and an interface 37, respectively.

Proper alignment of the non-contact eye pressure meter T with the eye E to be examined may be accomplished while the front eye part of the eye E to be examined illuminated by an external eye illuminating light L is imaged on the television camera 19, by the optical system comprising the objective lens 2, the window glass 3, the observation lens 14, the apertured mirror 15, the focusing lens 16 and the imaging lens 17 of the non-contact eye pressure meter T and is observed on the television monitor 26.

When the eye pressure measuring switch 34 is operated to measure the eye pressure after the non-contact eye pressure meter T has been properly aligned with the eye E to be examined, the plunger 8 is rotated through the command generating portion 33 and the control measuring portion 32 and the piston 5 is driven. The air pressure in the cylinder 4 gradually rises and an air stream is injected from the nozzle 1 to the cornea Ec. On the other hand, the parallel light emitted from the projection light source 10 and collimated by the projection lens 11 is projected onto the cornea Ec of the eye E to be examined, and the reflected hight from the cornea Ec is detected by the light-receiving element 13 via the hight-receiving lens 12. By the air pressure injected from the nozzle 1, the cornea Ec is changed from a convex surface to a concave surface, but the reflected light detected by the light-receiving element 13 assumes a maximum value when the cornea Ec becomes a substantially planar surface and therefore, by effecting the measurement of the lapse time at that point of time or the pressure measurement by the pressure sensor 150, the internal eye pressure IOP of the eye E to be examined is calculated by the control measuring portion 32 and is supplied to the data output control portion 30. The objective lens 2 is used in common for the eye pressure measurement and for the eye fundus observation which will be described later and therefore, the distance between the objective lens and the eye to be examined, i.e., the working distance, during the eye pressure measurement, is the same as the working distance during the eye fundus observation.

When the observation lens 14 is retracted out of the optical path as indicated by solid line, the image of the eye fundus Ef is formed on the television camera 19. At this time, the light emitted from the observation light source 24 passes through the infrared filter 23, the condenser lens 22, the ring slit plate 21, the light-intercepting plate 100 and the relay lens 20 and is reflected by the apertured mirror 15 bying at a position substantially conjugate with the ring slit plate 21 with respect to the relay lens 20, and is once imaged on the front eye part of the eye E to be examined via the window glass 3 and the objective lens 2 and thereafter illuminates the fundus Ef of the eye E to be examined and therefore, the image of the eye fundus is now displayed on the television monitor 26. At this time, the opening in the objective lens 2 is covered by the image of the light-intercepting plate 100 and thus, no harmful light is produced during the eye fundus photographing. Assuming that the eye fundus is illuminated by near-infrared light by the use of the infrared filter 23 and the television camera has sensitiviy for the same wavelength range as well, the pupil of the eye E to be examined will not shrink due to the illuminating light. Also, if the external eye illuminating light L is, for example, the invisible light by an infrared diode, it will be convenient for the same reason.

The light divider 18 comprises a half-mirror, a dichroic mirror or the like, and by the small fixation lamp 25 such as a light-emitting diode disposed substantially near the imaging plane of the television camera 19 being made movable in a plane perpendicular to the optic axis, the line of sight of the eye E to be examined can be conducted.

If the observation lens 14 is inserted onto the optical path and the alignment between the eye E to be examined and the apparatus is effected while the image of the front eye part of the eye E to be examined displayed on the television monitor 26 is being watched and then the observation lens 14 is shifted out of the optical path and the observation light source 24 is turned on, the image of the eye fundus is projected on the television monitor 26 and therefore, the fixation lamp 25 is operated so that the image of the disk can be seen. Then, the dimension D of the image of the disk and the dimension C of the image of the cup measured by the measuring means 27 are input from the command portion 31 to the operating portion 29 while the data selecting portion 28 is being operated, whereby the C/D ratio is calculated and stored.

Subsequently, the observation lens 14 is again inserted onto the optical path as indicated by dotted line and the alignment between the eye E to be examined and the apparatus is again confirmed, whereafter the non-contact eye pressure meter T is operated to measure the eye pressure of the eye E to be examined, and the result thereof can be arranged, for example, vertically and horizontally closely by the data output control portion 30 in relation to the C/D ratio. Also, the display by the display device 35 or the print-out by the printer 36 or a single output or plural outputs such as the outputs to other instruments via the interface 37 can be effected so that there may be provided areas distinguished by title letters such as right R and left L provided by conventional right and left eye detecting means, not shown.

Figure 2:
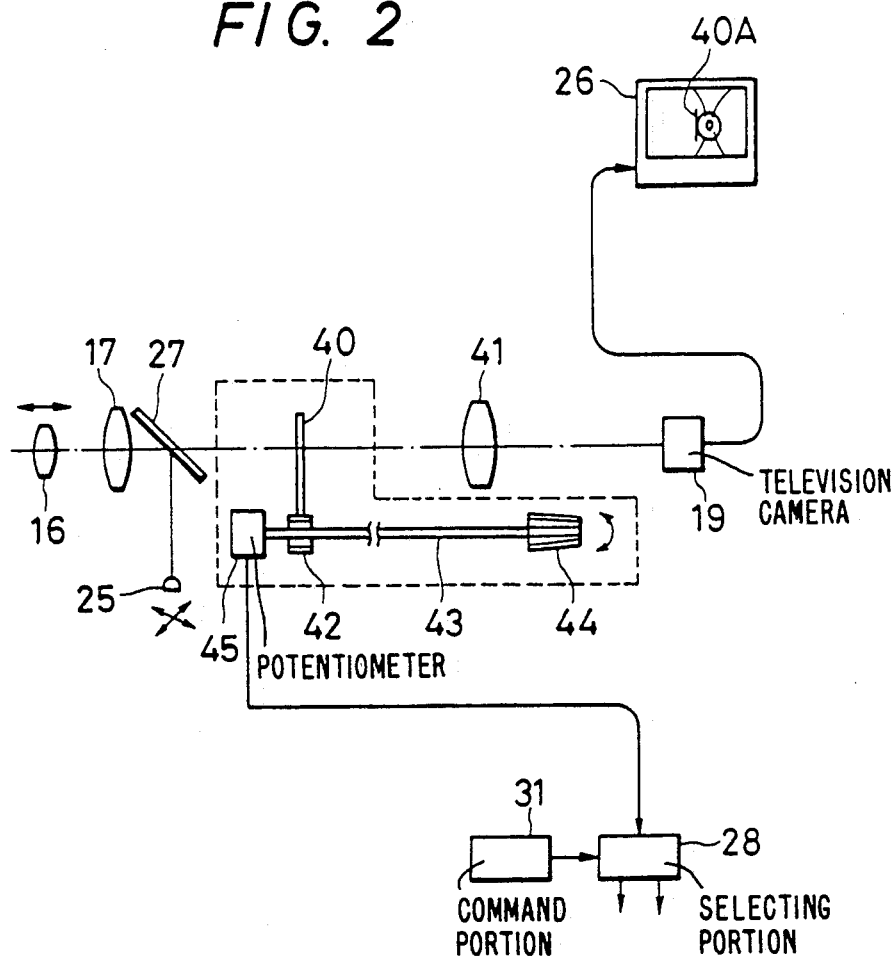
FIGS. 2 and 3 show an embodiment of a system for measuring the dimension regarding the disk portion of the image of an eye fundus.
Figure 3:
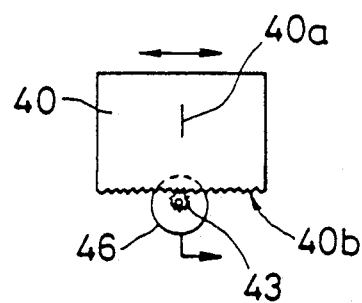

FIG. 2 shows another example of the measurement of the dimensions D and C of the image of the disk and the image of the cup. A transparent plate 40 having a line mark 40a as shown in FIG. 3 may be inserted forwardly of the television camera 19 of FIG. 1 and may be imaged on the television camera 19 via a re-imaging lens 41. The transparent plate 40 has a rack 40b provided at one end thereof, and by a knob 44 being turned via a pinion 42 meshing with the rack 40b and a shaft 43, the line mark 40a can be moved in a direction orthogonal to the plane of the drawing sheet of FIG. 2, i.e., the left to right direction as viewed in FIG. 3.

The image of the line mark 40a is superposed on the image of the eye fundus and is projected as a line mark image 40A on the television monitor 26 and therefore, by adjusting it to the end of the image of the disk or the image of the cup, the position thereof can be detected by a potentiometer 45 and supplied to the data selecting portion 28. In this case, of course, a command as to whether said end is the right end or the left end is effected in addition to the distinction between the image of the disk and the image of the cup. Further, if the transparent plate 40 is rotated in any direction about the optic axis within the necessary range, the dimensions of the images of the disk and cup in any meridian direction can be measured.

Figure 4:
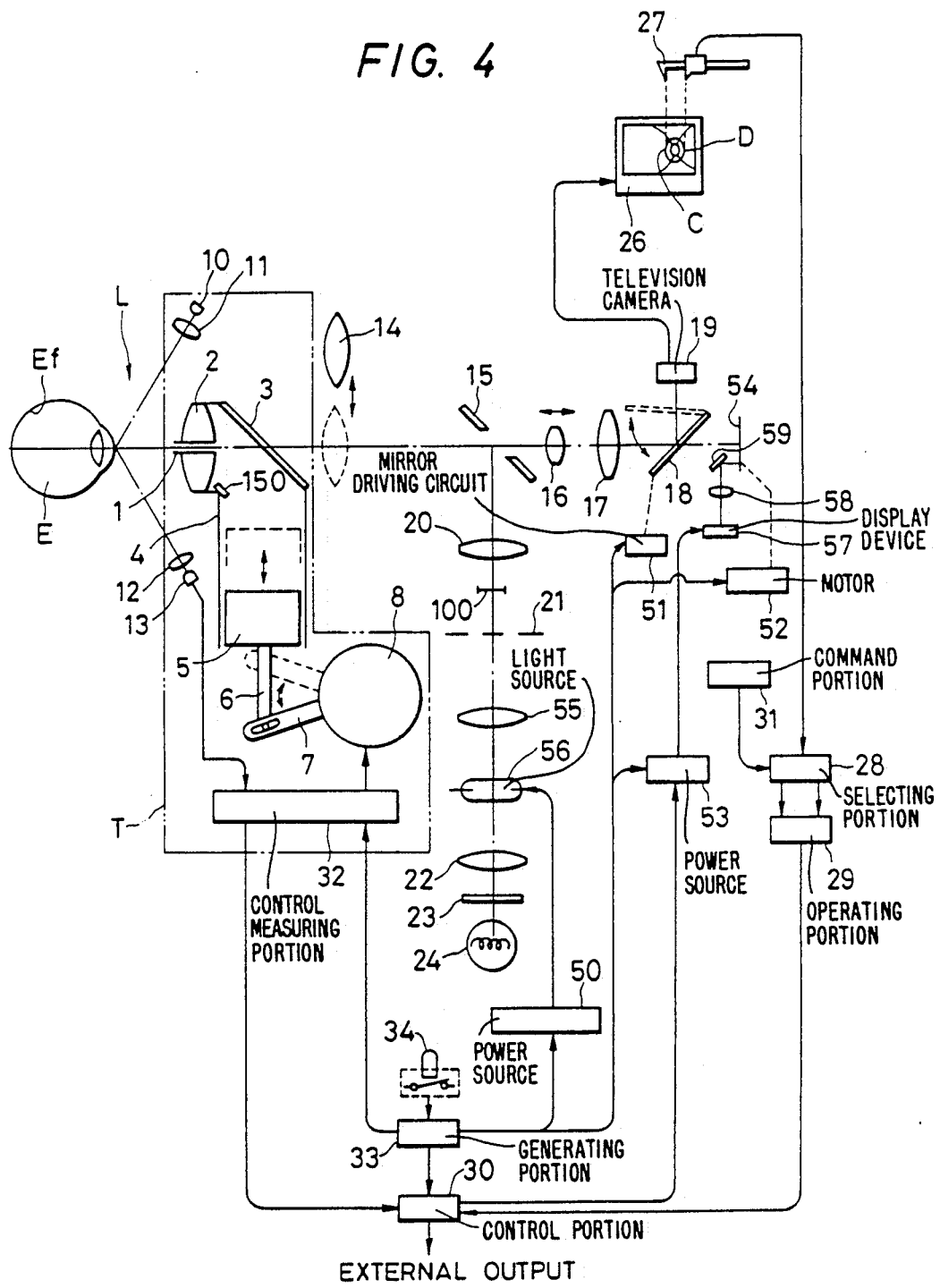
FIG. 4 shows an embodiment for photographing the value of the eye pressure and the C/D value into a film with the image of the eye fundus.

FIG. 4 shows an embodiment in which the eye pressure value of the eye to be examined, the value of the C/D ratio and the image of the eye fundus are recorded on the same recording medium. In FIG. 4, reference numerals similar to those in FIG. 1 designate similar members. Reference numeral 50 designates a power source for photo-taking, reference numeral 51 denotes a mirror driving circuit, reference numeral 52 designates a motor, reference numeral 53 denotes a power source for displaying, reference numeral 54 designates a film, reference numeral 55 denotes a condenser lens, reference numeral 56 designates a light source for photo-taking, reference numeral 57 denotes a display device for recording, reference numeral 58 designates a lens, and reference numeral 59 denotes a mirror.

To photograph and record the image of the eye fundus, the pivotable mirror 18 may be moved up and the light source 56 for photo-taking may be turned on for a very short time, whereby the image by visible light may be recorded on the film 54 provided at a position conjugate with television camera 19. During the observation of the eye fundus in this case, the line of sight of the eye E to be examined can be conducted by the small fixation lamp such as a light-emitting diode disposed substantially near the imaging plane of the television camera 19 being made movable.

Now, in the eye fundus image observing state, the diameter dimension D of the disk and the diameter dimension C of the cup are measured by the measuring means 27 on the image of the eye fundus displayed on the television monitor 26, and are sent to the operating portion 29 via the data selecting portion 28 in accordance with the direction from the command portion 31 to carry out the calculation of $C \div D$, the result of which is stored. Subsequently, the photographing of the image of the eye fundus and the measurement of the eye pressure are carried out, and these are controlled so that the photographing and then the measurement of the eye pressure are carried out at a very short time interval in accordance with the command.

Figure 5:
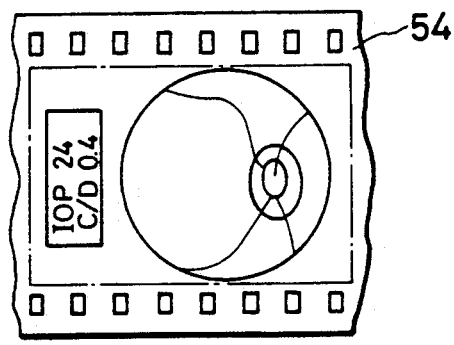
FIG. 5 shows a film on which the value of the eye pressure and the C/D value are recorded with the image of the eye fundus.

That is, when the measuring switch 34 is depressed, the contact thereof is closed and the command generating portion 33 operates the mirror driving circuit 51 to move the pivotable mirror 18 upwardly, while it operates the power source 50 for photo-taking to turn on the light source 56 for photo-taking, whereby the image of the eye fundus Ef is recorded on the film 54. Further, the command generating portion 33 also operates the non-contact eye pressure meter T and the measured value of the eye pressure is supplied to the data output control portion 30 and is displayed on the display device 57 via the power source 53 for displaying which effects the control of light emission, with the recorded content of the operating portion 29, and is imaged and recorded near the eye fundus image on the film 54 by the lens 58 and the mirror 59. Further, after this recording has been completed, the film advance motor 52 is operated to advance the film 54 by an amount corresponding to one frame. FIG. 5 shows an example of the record on the film 54. As shown, the value of the eye pressure and the numerical data of the C/D ratio are photographed near the eye fundus image.

It is because the photographing which can be accomplished within the order of 1 mS is executed before the deformation and slight movement of the eyeball by the injection of air for the measurement of the eye pressure and the measurement of the eye pressure is also terminated before there occurs any misalignment due to the blinking or the slight movement of the eyeball caused by the stimulus of light that the photographing and the measurement of the eye pressure are carried out in the above-mentioned order.

Figure 6:
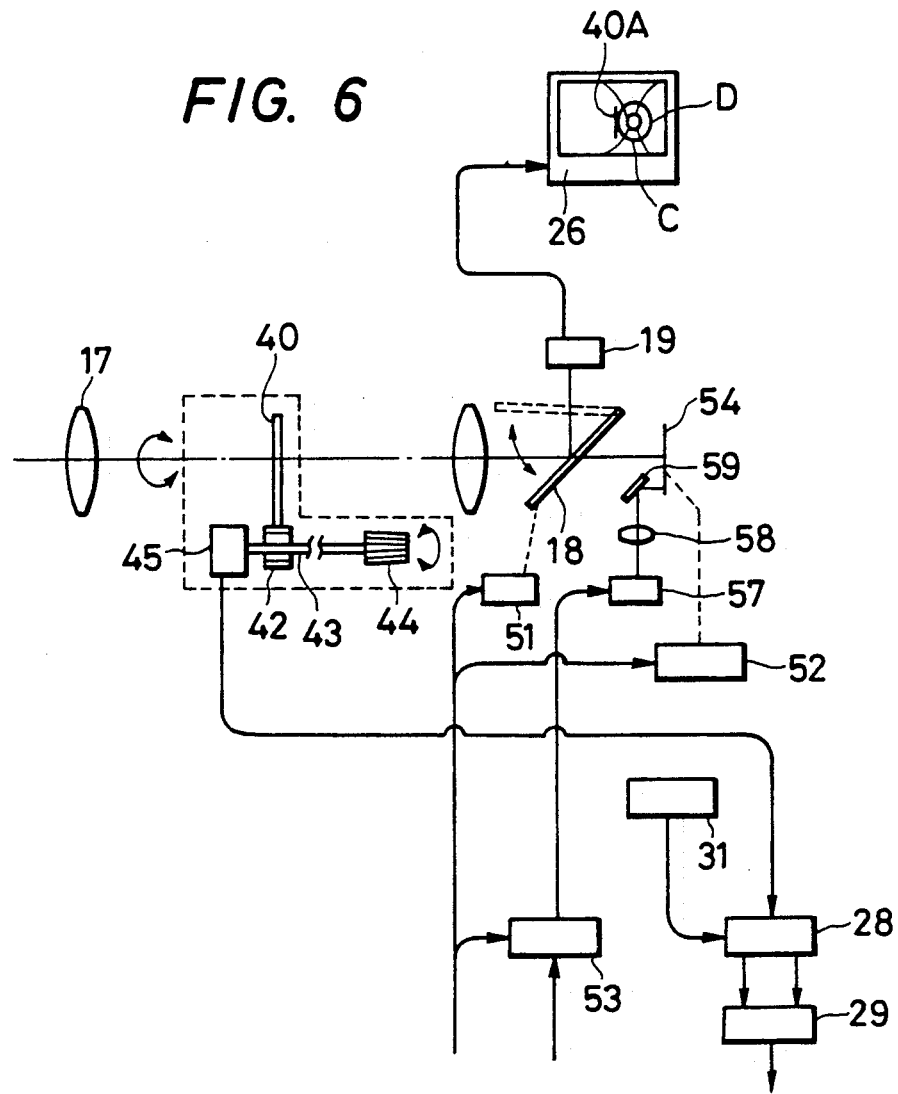
FIG. 6 shows an embodiment including the system for measuring the dimension regarding the disk portion of the image of the eye fundus.

FIG. 6 shows a modification including a dimension measuring system provided with the members 40-45 shown in FIG. 2.

Figure 7:
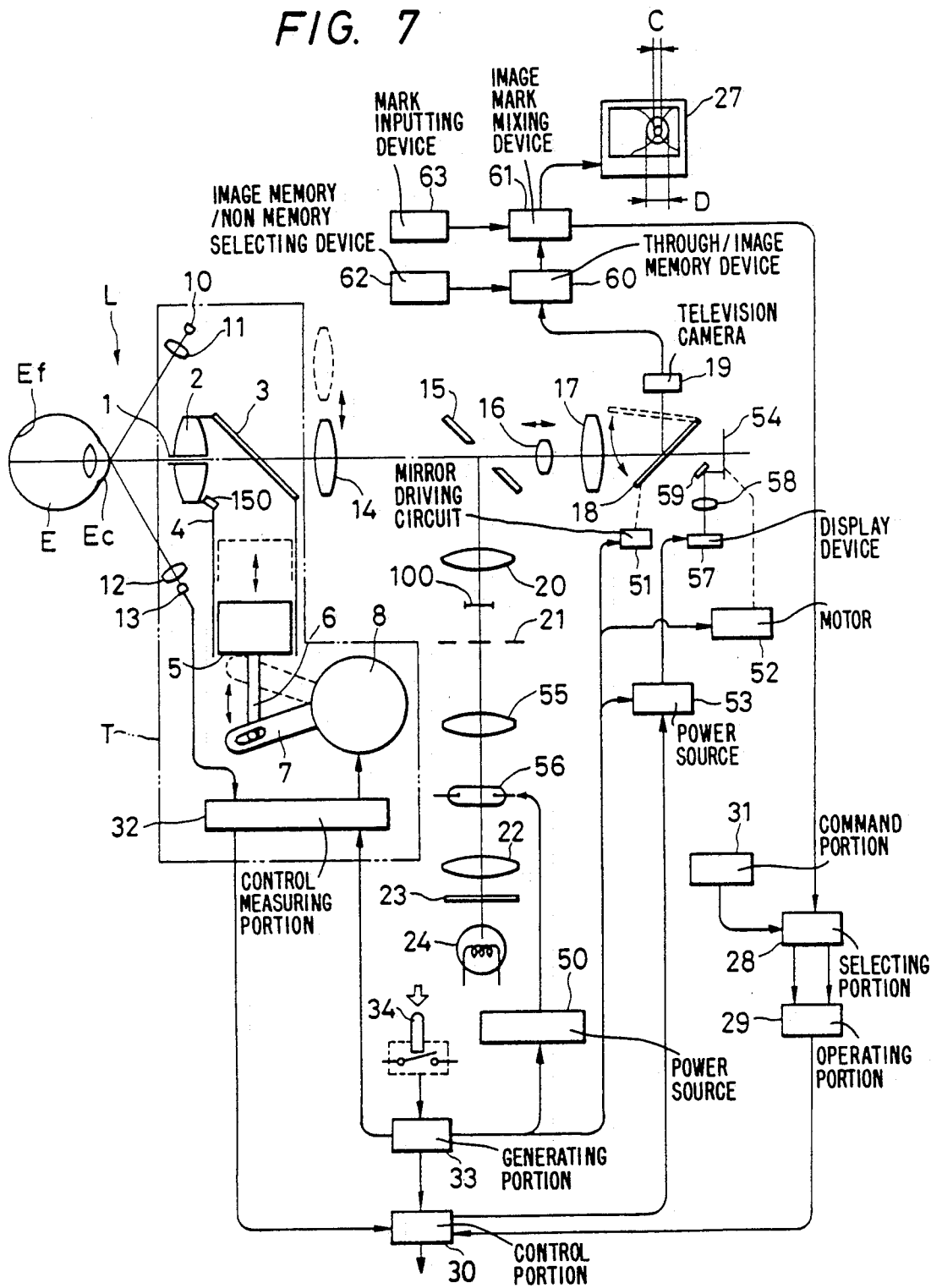
FIG. 7 shows an embodiment in which an image memory is provided between a television camera and a television monitor.

FIG. 7 shows an embodiment in which an image memory is provided between the television camera and the television monitor.

Reference numeral 60 designates a through/image memory device, reference numeral 61 denotes an image-mark mixing device, reference numeral 62 designates an image memory/non-memory selecting device, and reference numeral 63 denotes a mark inputting device. The output of the television camera 19 may be input to the television monitor 27 through the through-/image memory device 60 and the image-mark mixing device 61 to project the image of the eye E to be examined onto the television monitor. The image memory/-non-memory selecting device 62 is connected to the through/image memory device 60 and the mark inputting device 63 is connected to the image-mark mixing device 61, and they are used when the region of the eye E to be examined is measured.

The output of the image-mark mixing device 61 is supplied to the data selecting portion 28.

Proper alignment of the non-contact eye pressure meter T with the eye E to be examined may be accomplished while the front eye part of the eye E to be examined emitted by the external eye illuminating light L is imaged on the television camera 19 with the pivotable mirror 18 moved down and through the optical system comprising the objective lens 2, the window glass 3, the observation lens 14, the apertured mirror 15, the focusing lens 16 and the imaging lens 17 of the non-contact eye pressure meter T and is observed on the television monitor 27 with the through/image memory device 60 brought into the through state.

Now, the eyeball of the eye to be examined is very ready to move when the diameter dimension D of the disk and the diameter dimension C of the cup are measured on the eye fundus image displayed on the television monitor 27 in the eye fundus image observing state and therefore, the through/image memory device 60 is brought into the image memory recording state by the memory/non-memory selecting device 62 and at that point of time, the eye fundus image is fixed and displayed on the television monitor 27. The mark is then input from the mark inputting device 63 connected to the image-mark mixing device 61 to any position on the screen of the television monitor 27. In that case, the positional information of the mark displayed on the television monitor 27 by the mark inputting device 63 is controlled by the command portion 31 and is supplied to the operating portion 29 via the data selecting portion 28, whereby the diameter dimension D of the disk and the diameter dimension C of the cup are calculated, and then the calculation of $C \div D$ is carried out, and the result thereof is stored. When the measurement of the diameter dimension D of the disk and the diameter dimension C of the cup is terminated, the through/image memory device 60 is placed in the through state.

In the foregoing description, as the means for recording the eye fundus image, a magnetic recording system including photoelectric converting means such as a so-called electronic camera may be used instead of directly recording on the film 54. The output from the data output control portion 30 can not only be used for recording, but also can be put out to a separate machine.

Further, instead of carrying out all of the measurement of the eye pressure, the measurement of the C/D ratio and the photographing of the eye fundus, it is also possible to carry out, for example, only the measurement of the eye pressure and the photographing of the eye fundus or only the measurement of the C/D ratio and the photographing of the eye fundus.

In addition, it is also possible to carry out the measurement and recording of the diameter of the pupil and the diameter of the cornea during the external eye observation.

Figure 8:
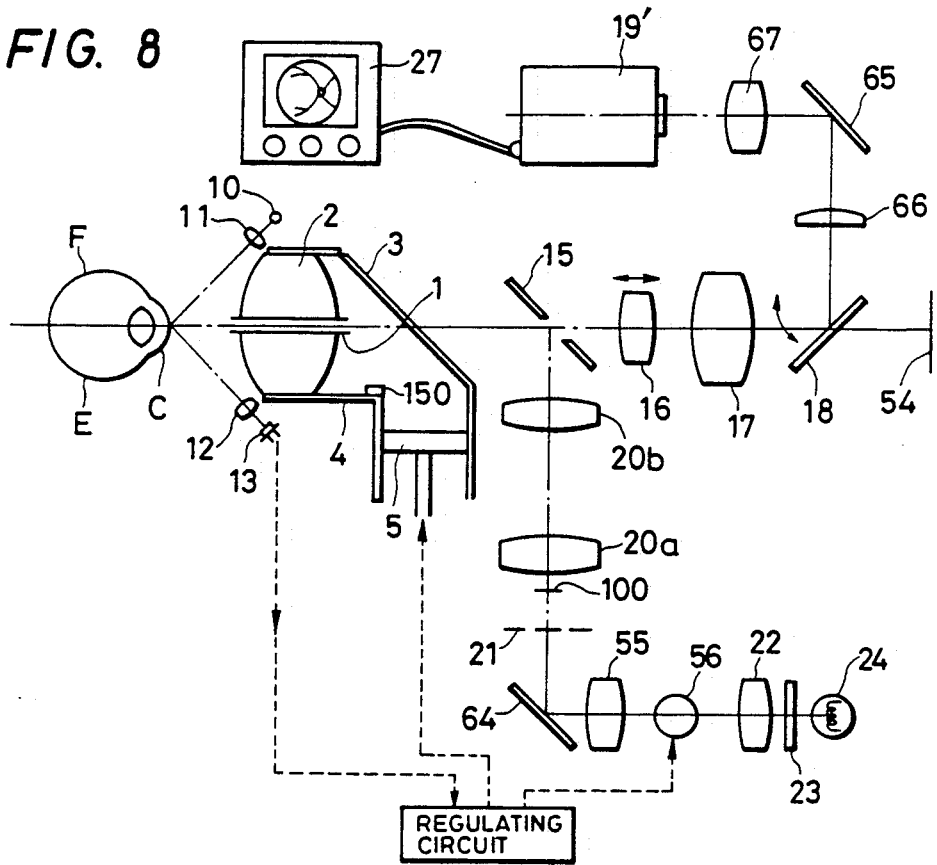
FIG. 8 shows an embodiment which is provided with a control circuit for providing for the timing of eye fundus photographing and eye pressure measurement.

FIG. 8 shows an embodiment provided with a control circuit so that the photographing of the eye fundus may be completed before the deformation of the cornea by the eye pressure measuring means. In FIG. 8, reference numerals similar to those in FIG. 1 designate similar members. Reference numeral 19' designate image pickup means, reference characters 20a and 20b denote relay lenses, reference numerals 64 and 65 designate mirrors, reference numeral 66 denotes a field lens, and reference numeral 67 designates a relay lens.

In the measurement of the eye pressure and the photographing of the eye fundus, the eye E to be examined must be in its optimum condition and for example, when the photographing of the eye fundus F is carried out, the eyelids are closed and the direction of the line of sight of the eye is indefinite and the eyeball also moves. On the other hand, when air is blown for the measurement of the eye pressure, the cornea C is deformed and the eyelids are closed and the eyeball also moves, thus hampering other functions with each other.

Figure 9:
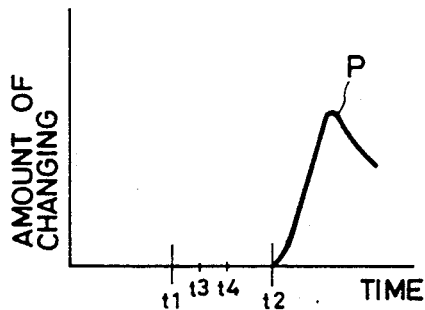
FIG. 9 illustrates the timing.

In the present apparatus, when the examiner operates the operating means such as a push button switch, the cornea C begins to be deformed in time t1 after the generation of a piston start signal for the measurement of the eye pressure as shown in FIG. 9, and the light emission for the photographing of the eye fundus may be terminated between t3 to t4 in time t2 during which the photographing of the eye fundus F becomes inappropriate. That is, the output of the light-receiving element 13 enters a control circuit 200, which thus controls the light emission of the light source 56 for photo-taking and the driving of the piston 5. For example, assuming that the deformation of the cornea C begins in about 15 mS after the generation of a trigger signal for piston start and the light emission of the light source 56 for photo-taking is terminated in about 2 mS after the generation of the trigger signal, the control circuit 200 controls so that the trigger signal of the piston 5 is not generated in at least 13 mS before the trigger signal of the light source 56 for photo-taking.

Figure 10:
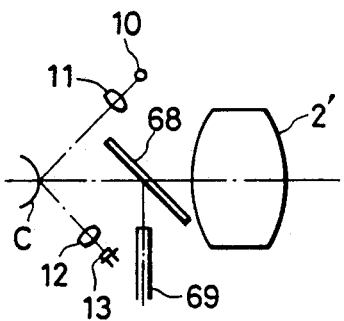
FIGS. 10 to 13 show modifications of the connecting means for the eye pressure measuring system and the eye fundus photographing system.

Now, FIG. 10 and so on show a method of compling the eye fundus photographing system and the eye pressure measuring system. In FIG. 10, a planar glass 68 is obliguely disposed forwardly of the objective lens 2' and the air from a nozzle 69 is blown against the cornea C through the planar glass 68. In this case, the eye fundus photographing light beam is transmitted through the planar glass 68, but where the planar glass 68 is not a light-transmitting member, the planar glass 68 may be caused to escape out of the optical path during photography and may be inserted into a predetermined position in the optical path during the measurement of the eye pressure.

Figure 11:
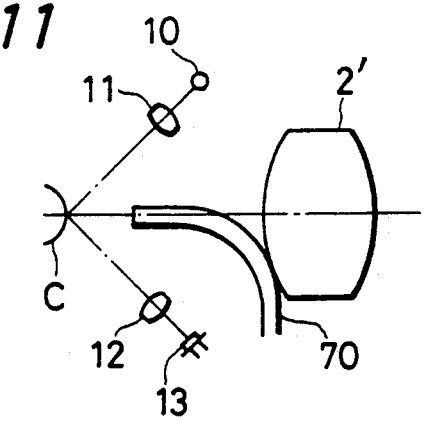

FIG. 11 shows an arrangement in which a nozzle 70 is directly disposed forwardly of the objective lens 2' and may be moved out of the optical path as required.

Figure 12:
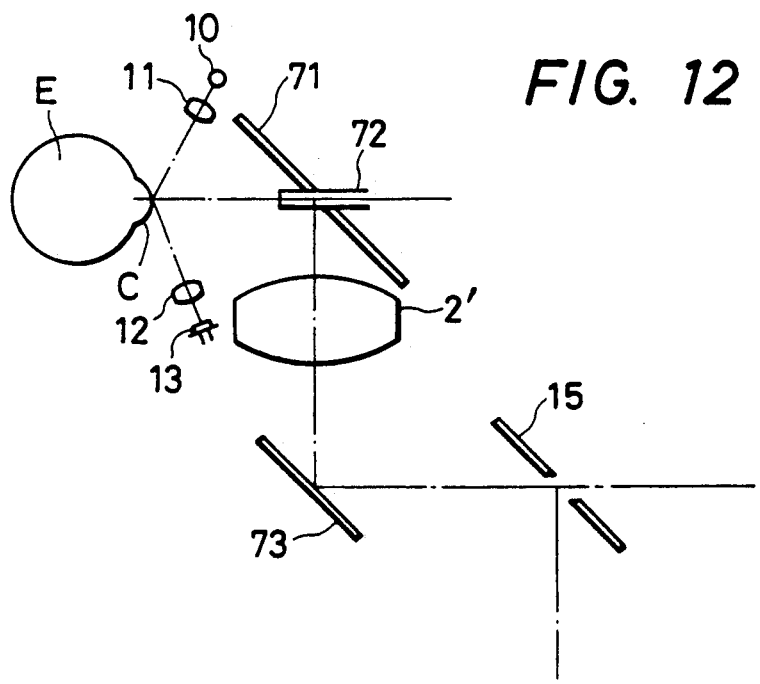

FIG. 12 shows an example in which the optic axis of the objective lens 2' is apparently bent with respect to the optic axis of the eye E to be examined and an obliquely disposed light reflecting member 71 is provided with a hole in which a nozzle 72 is inserted. In this example, a mirror 73 provided below the objective lens 2' and subsequent members are similar to those in FIG. 8.

Figure 13:
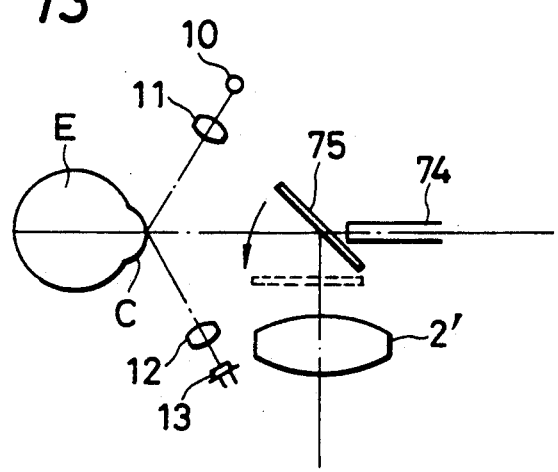

FIG. 13 shows an example in which an inverting mirror 75 is obliquely disposed forwardly of a nozzle 74. In this example, the objective mirror 2' and subsequent members are similar to those in FIG. 12.

In the foregoing description, the photograhing of the eye fundus and the measurement of the eye pressure have been described as taking place in operative association with each other, but actually, the two means may preferably be designed so as to be also capable of functioning independently of each other so that for example, the measurement of the eye pressure can be effected a plurality of times to thereby find an optimum value and only the photographing of the eye fundus can be executed even when the examiner fails in the photographing of the eye fundus.

Also, the photographing of the eye fundus is carried out before the deformation of the cornea in the measurement of the eye pressure, but where it is detected that deformation of the cornea has already begun when the photographing of the eye fundus is effected with the aid of the signal of the light-receiving device 13, it is preferable that the photographing be interrupted. This is because in such case, the probability at which a clear image is not obtained due to the deformation of the cornea is great or blinking sometimes provides the deformation signal of the cornea and likewise in such case, a good image cannot be expected to be obtained.

We claim:
1. An ophthalmic examining apparatus, comprising:
   eye fundus information detecting means for detecting information relating to the eye fundus and including an objective lens begin positionable opposite an eye to be examined;
   fluid discharging means for discharging fluid against the eye to be examined, said fluid discharging means including fluid pressure varying means for varying fluid pressure over time, said fluid discharging means further including a blowing nozzle substantially coaxial with an optical axis of said objective lens;
   cornea deformation detecting means for detecting deformation of a cornea of the eye to be examined caused by said fluid discharged by said fluid discharging means, said cornea deformation detecting means including light projection means for projecting a light flux to the cornea and light receiving means for receiving a light flux reflected by the cornea;
   detecting means for detecting at least one of internal pressure information on the internal pressure in said fluid discharging means and time information relating to the length of time of discharging of said fluid discharging means; and
   calculating means for calculating data of an eye pressure of the eye to be examined on the basis of information of said cornea deformation detecting means and at least one of said internal pressure information and said time information.

2. An ophthalmic examining apparatus according to claim 1, wherein said eye fundus information detecting means is provided with a measuring means for measuring a size representing a disk portion of the eye fundus.

3. An ophthalmic examining apparatus according to claim 1, wherein said objective lens is provided with a through-hole positioned near a fluid outlet of said blowing nozzle.

4. An ophthalmic examining apparatus according to claim 3, wherein said objective lens is operably associated with an illuminating means for illuminating the eye to be examined and said eye fundus information detecting means, and wherein said ophthalmic examining apparatus further comprises light-intercepting means for shielding said through-hole from illuminating light in said illuminating means, and said light-intercepting means is substantially optically conjugate with that end of the through-hole of said objective lens which is remote from the eye to be examined.

5. An ophthalmic examining apparatus according to claim 1, wherein said calculating means includes time calculating means for calculating data of the eye pressure on the basis of the time information from a reference time to a time when the predetermined deformation of the cornea is detected.

6. An ophthalmic examining apparatus according to claim 1, wherein said calculating means includes internal pressure calculating means for calculating data of the eye pressure on the basis of internal pressure in said fluid discharging means when a predetermined deformation of the cornea is detected.

7. An ophthalmic examining apparatus according to claim 1, further having front eye part observation means for observing a front eye part of the eye to be examined.

8. An ophthalmic examining apparatus according to claim 7, further comprising an imaging lens inserted in an optical path of the objective lens during the observation of the front eye part.

9. An ophthalmic examining apparatus according to claim 7, wherein said eye fundus information detecting means and said front eye part observation means are provided with means for visualizing the image of the fundus of the eye to be examined and the image of the front eye part of the eye to be examined when illuminated by an invisible light.

10. An ophthalmic examining apparatus according to claim 1, wherein said eye fundus information detecting means is provided with means for visualizing the image of the fundus of the eye to be examined when the fundus of the eye to be examined is illuminated by an infrared light.

11. An ophthalmic examining apparatus according to claim 1, further comprising means for forming an image of the fundus of the eye to be examined and data of the eye pressure on a single surface.

12. An ophthalmic examining apparatus according to claim 2, further comprising means for forming an image of the fundus of the eye to be examined and data of at least one of the eye pressure and the result of the measurement by said measuring means on a single surface.

13. An ophthalmic examining apparatus according to claim 12, wherein said eye fundus information detecting means is provided with eye fundus photographing means for photographing the fundus of the eye to be examined and wherein the image of the fundus of the eye to be examined, the data of eye pressure, and the result of the measurement by said measuring means are all recorded on the same recording medium.

14. An ophthalmic examining apparatus according to claim 7, wherein said eye fundus information detecting means and said front eye part observation means have a common television camera and a common television monitor, and an image memory is provided between said television camera and said television monitor.

15. An ophthalmic examining apparatus according to claim 14, further comprising image-mark mixing means positioned between said image memory and said television monitor.

16. An ophthalmic examining apparatus according to claim 1, wherein a reflecting member is provided in an optical path between said objective lens means and the eye to be examined, and the information of the eye fundus is detected by way of said reflecting member and said objective lens.

17. An ophthalmic examining apparatus according to claim 16, wherein the fluid outlet of said blowing nozzle is positioned rearwardly of said reflecting member, and said reflecting member is moved out of the optical path during the measurement of the eye pressure.

18. An ophthalmic examining apparatus according to claim 16, wherein said reflecting member is provided with a through-hole positioned near the blowing nozzle of said fluid discharging means.

19. An ophthalmic examining apparatus according to claim 1, wherein a transparent plate is provided in the optical path between said objective lens means and the eye to be examined, and said fluid discharging means is disposed in an optical path reflected by said transparent plate.

20. An ophthalmic examining apparatus according to claim 1, wherein the working distance during the measurement of the eye pressure is the same as the working distance during the detection of the eye fundus information.

21. An ophthalmic examining apparatus comprising:
eye fundus information detecting means, with an objective lens, for detecting information of an eye fundus, said objective lens being positionable opposite an eye to be examined;
fluid discharging means for discharging fluid against the eye to be examined, said fluid discharging means including pressure varying means for varying fluid pressure over time, said fluid discharging means further including a blowing nozzle substantially coaxial with an optical axis of the objective lens;
cornea deformation detecting means for detecting deformation of a cornea of the eye to be examined caused by said fluid discharged by said fluid discharging means, said cornea deformation detecting means being provided with a light source for irradiating the cornea of the eye to be examined and a sensor for receiving the reflected light from the cornea of the eye to be examined;
detecting means for detecting at least one of internal pressure information on the internal pressure in said fluid discharging means and time information relating to the length of time of discharging of said fluid discharging means;
calculating means for calculating data of an eye pressure of the eye to be examined on the basis of information of said cornea deformation detecting means and at least one of said internal pressure information and said time information of said fluid discharging means; and control means, having a switch, for enabling detection of the information of the eye fundus without a substantial cornea deformation prior to a measurement of the eye pressure.

22. An ophthalmic examining apparatus according to claim 21, wherein said eye fundus information detecting means is provided with a measuring means for measuring a size representing a disk portion of the eye fundus.

23. An ophthalmic examining method having the steps of:
  detecting information of a fundus of an eye to be examined through an objective lens means opposed to the eye to be examined;
  discharging fluid against an eye to be examined along an axis substantially coaxial with an optical axis of said objective lens means after detecting the information of the fundus of the eye to be examined;
  changing a pressure of the fluid over time;
  optically detecting a deformed state of the cornea of the eye to be examined caused by the fluid;
  detecting at least one of internal pressure information of the discharging fluid and time information relating to the length of time of the discharging of the fluid against the eye;
  calculating a data of an eye pressure of the eye to be examined on the basis of one of the internal pressure information and the time information of the fluid when a predetermined deformation of the cornea is detected.

* * * * *

UNITED STATES PATENT AND TRADEMARK OFFICE
CERTIFICATE OF CORRECTION

PATENT NO. : 4,991,584

DATED : February 12, 1991

INVENTOR(S) : Kazunobu Kobayashi, et al

It is certified that error appears in the above-identified patent and that said Letters Patent is hereby corrected as shown below:

COLUMN 3:

Line 27, "reflected hight" should read --reflected light--.

Line 29, "hight-receiving" should read --light-receiving--.

Line 54, "bying" should read --lying--.

Line 67, "sensitiviy" should read --sensitivity--.

Signed and Sealed this

Twentieth Day of October, 1992

Attest:

DOUGLAS B. COMER

*Attesting Officer*       *Acting Commissioner of Patents and Trademarks*